ns Patent [19] [11] 4,410,732
Ozawa et al. [45] Oct. 18, 1983

[54] PHENYL KETONE DERIVATIVES

[75] Inventors: Kiyomi Ozawa; Yasuyuki Nakajima; Makoto Tsugeno, all of Funabashi, Japan

[73] Assignee: Nissan Chemical Industries Ltd., Tokyo, Japan

[21] Appl. No.: 387,778

[22] Filed: Jun. 14, 1982

[30] Foreign Application Priority Data

Jul. 7, 1981 [JP] Japan ............... 56-105020

[51] Int. Cl.³ .......................... C07C 49/825
[52] U.S. Cl. .................. 568/337; 568/42; 568/329; 568/331; 260/465 D
[58] Field of Search .......... 568/337, 329, 331, 42, 568/442; 260/465 D

[56] References Cited

U.S. PATENT DOCUMENTS 3,967,949  7/1976  Benefiel et al. .......... 568/337
3,978,132  8/1976  Houlihan et al. ......... 568/331
4,140,792  2/1979  Surenberg .............. 568/379

FOREIGN PATENT DOCUMENTS 862133   of 0000  Belgium .
2905687  8/1980  Fed. Rep. of Germany ...... 568/331

OTHER PUBLICATIONS

Rico et al., Tetrahedron Letters, vol. 22, pp. 323-326 (1981).

*Primary Examiner*—James H. Reamer
*Attorney, Agent, or Firm*—Oblon, Fisher, Spivak, McClelland & Maier

[57] ABSTRACT

Ketone derivatives represented by the general formula (I)

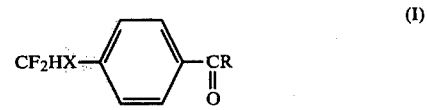

where R is —$CH_2R^1$ (where $R^1$ is a hydrogen atom or an alkyl group), a halogen-substituted alkyl group, a cyano-substituted alkyl group, a cyclopropyl group,

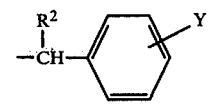

(where $R^2$ is a hydrogen atom or an alkyl group and Y is a hydrogen atom or a halogen atom) or

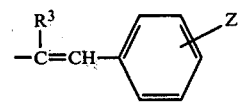

(where $R^3$ is a hydrogen atom, an alkyl group, a phenyl group or a halogen-substituted phenyl group, and Z is a hydrogen atom or a halogen atom), and X is an oxygen atom or a sulfur atom.

9 Claims, No Drawings

PHENYL KETONE DERIVATIVES

BACKGROUND OF THE INVENTION

1. Field of the Invention

The present invention relates to novel ketone derivatives useful as intermediates for the production of agricultural or horticultural insecticides.

2. Description of the Prior Art

The ketone derivatives of the present invention are novel compounds not disclosed in any prior art literatures.

SUMMARY OF THE INVENTION

The present invention provides ketone derivatives (hereinafter referred to as "compounds of the present invention") represented by the general formula (I)

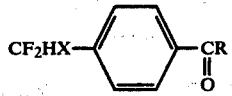
(I)

where R is —$CH_2R^1$ (where $R^1$ is a hydrogen atom or an alkyl group), a halogen-substituted alkyl group, a cyano-substituted alkyl group, a cyclopropyl group,

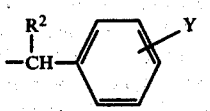

(where $R^2$ is a hydrogen atom or an alkyl group and Y is a hydrogen atom or a halogen atom) or

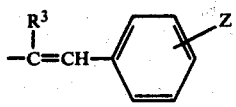

(where $R^3$ is a hydrogen atom, an alkyl group, a phenyl group or a halogen-substituted phenyl group, and Z is a hydrogen atom or a halogen atom), and X is an oxygen atom or a sulfur atom.

DETAILED DESCRIPTION OF THE PREFERRED EMBODIMENTS

The compounds of the present invention are useful as intermediates for the production of agricultural or horticultural insecticides. The usefulness will be described briefly below:

Reaction scheme (1):

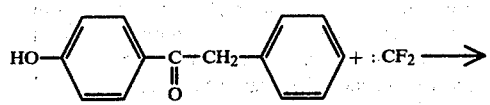

Reaction scheme (2):

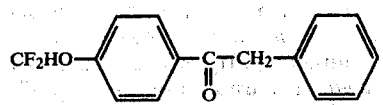

-continued

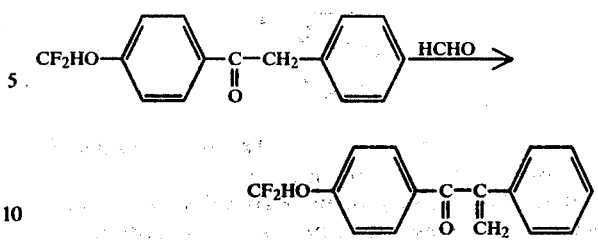

Reaction scheme (3)

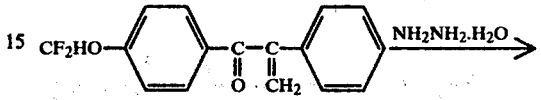

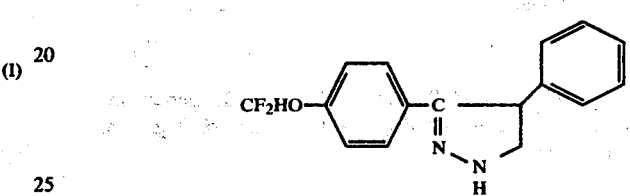

Reaction scheme (4)

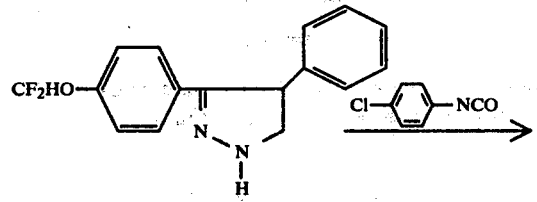

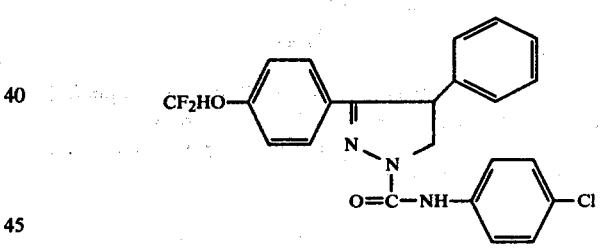

Namely, 4'-difluoromethoxy-2-phenylacetophenone obtainable by the reaction of the scheme (1) is one of the compounds of the present invention. Whereas, the product obtainable by the subsequent reactions of the schemes (2), (3) and (4), i.e. 1-(4-chlorophenylcarbamoyl)-3-(4-difluoromethoxyphenyl)-4-phenyl-2-pyrazoline (described in Japanese Patent Application No. 21717/81), has strong insecticidal activities against a wide variety of insects harmful to agricultural or horticultural plants.

Preferred ketone derivatives of the present invention are represented by the general formula (II)

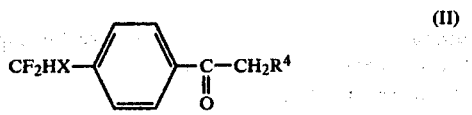
(II)

where $R^4$ is a hydrogen atom, an alkyl group having from 1 to 9 carbon atoms or

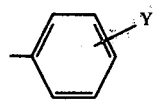

(where Y is a hydrogen atom or a halogen atom), and X is an oxygen atom or a sulfur atom.

Now, the processes for the preparation of the compounds of the present invention will be described.

Reaction scheme (5):

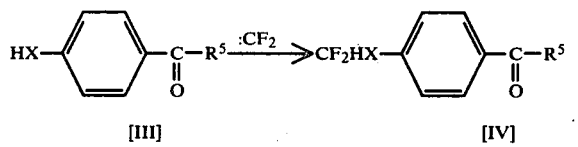

where $R^5$ is —$CH_2R^1$ (where $R^1$ is a hydrogen atom or an alkyl group), a halogen-substituted alkyl group, a cyclopropyl group,

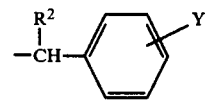

(where $R^2$ is a hydrogen atom or an alkyl group, and Y is a hydrogen atom or a halogen atom), or

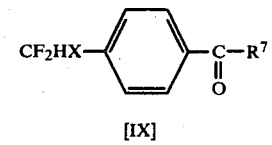

(where $R^3$ is a hydrogen atom, an alkyl group, a phenyl group or a halogen-substituted phenyl group and Z is a hydrogen atom or a halogen atom), and X is an oxygen atom or a sulfur atom.

Reaction scheme (6):

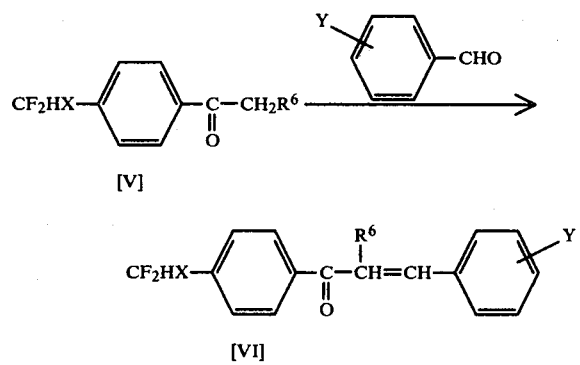

where $R^6$ is a hydrogen atom or an alkyl group, X is an oxygen atom or a sulfur atom, and Y is a hydrogen atom or a halogen atom.

Reaction scheme (7):

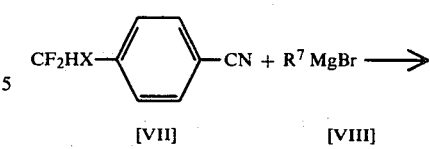

[VII]    [VIII]

CF$_2$HX—⟨benzene⟩—C—$R^7$
                   ‖
                   O

[IX]

where $R^7$ is —$CH_2R^1$ (where $R^1$ is a hydrogen atom or an alkyl group), a cyclopropyl group or $R^2$
|
—CH—⟨benzene⟩—Y (where $R^2$ is a hydrogen atom or an alkyl group and Y is a hydrogen atom or a halogen atom), and X is an oxygen atom or a sulfur atom.

Namely, an acylphenol or acylthiophenol represented by the general formula [III] is reacted with difluorocarbene in accordance with the reaction scheme (5), whereby a phenylketone derivative represented by the general formula [IV] is obtainable. The difluorocarbene used in this reaction can be readily prepared by a known method, for instance, by a method in which Freon 22 gas is used (T. G. Miller and J. W. Thanassi, J. Org. Chem., 25, 2009 (1960), a method in which dibromodifluoromethane is used (R. F. Clark and J. H. Simons., J. Am. Chem. Soc., 77, 6618 (1955)) or a method in which difluorocarbene is generated from CClF$_2$COONa, (CH$_3$)$_3$SnCF$_3$, etc. For instance, it is possible to obtain a phenylketone derivative represented by the general formula [IV] in high yield by treating the compound represented by the general formula [III] with Freon 22 gas in an aqueous alkaline solution and dioxane. In this case, the reaction may be conducted at a temperature from room temperature to the refluxing temperature of the solvent. However, the reaction temperature is preferably from 40° to 80° C. As an alternative method of using Freon 22 gas, difluorocarbon obtained by introducing Freon 22 gas into a heated aqueous alkaline solution and dioxane, may be blown into a mixed solution comprising the compound represented by the general formula [III] and an aqueous alkaline solution and dioxane. In this case, the reaction temperature may be at room temperature, and the reaction proceeds with generation of heat.

In the reaction scheme (6), an alcohol such as ethanol is used as the solvent, and an aqueous solution of a base such as sodium hydroxide is added to carry out the reaction with the aldehyde derivative. The reaction can adequately be carried out at room temperature.

In the reaction scheme (7), an ether such as ethyl ether is used as the solvent, and a Grignard reagent represented by the general formula [VIII] is reacted with a benzonitrile derivative represented by the general formula [VII]. Thereafter, the reaction mixture is treated in a usual manner for a Grignard reaction, whereby the desired phenylketone derivative is obtainable.

Now, the compounds of the present invention will be presented in the following Table 1. However, the present invention is not limited to these specific compounds.

TABLE 1

$$CF_2HX-\phenyl-\underset{O}{\overset{\|}{C}}-R$$

| Compound No. | X | R | b.p., m.p. or $n_D^{20}$ |
|---|---|---|---|
| 1 | O | —CH$_3$ | b.p. 98–100° C./3 mmHg |
| 2 | O | —CH$_2$CH$_3$ | b.p. 108–109° C./3 mmHg |
| 3 | O | —CH(CH$_2$)(CH$_2$) (cyclopropyl) | $n_D^{20}$ 1.5150 |
| 4 | O | —CH$_2$CH(CH$_3$)$_2$ | b.p. 108–110° C./0.5 mmHg |
| 5 | O | —(CH$_2$)$_4$CH$_3$ | |
| 6 | O | —CH$_2$C(CH$_3$)$_3$ | |
| 7 | O | —(CH$_2$)$_6$CH$_3$ | m.p. 30–35° C. |
| 8 | O | —(CH$_2$)$_8$CH$_3$ | |
| 9 | O | —(CH$_2$)$_4$CN | $n_D^{20}$ 1.5045 |
| 10 | O | —CH$_2$—Ph | m.p. 52–60° C. |
| 11 | O | —CH$_2$—C$_6$H$_4$—F | m.p. 50–56° C. |
| 12 | O | —CH$_2$—C$_6$H$_4$—Cl | m.p. 74–76° C. |
| 13 | O | —CH$_2$—C$_6$H$_4$—Br | |
| 14 | O | —CH(CH$_3$)—Ph | |
| 15 | O | —CH(CH$_2$CH$_3$)—Ph | |
| 16 | O | —CH(CH(CH$_3$)$_2$)—Ph | $n_D^{20}$ 1.5312 |
| 17 | O | —CH(CH(CH$_3$)$_2$)—C$_6$H$_4$—Cl | |
| 18 | O | —CH=CH—Ph | m.p. 96–98° C. |
| 19 | O | —CH=CH—C$_6$H$_4$—Cl | m.p. 114–115° C. |
| 20 | O | —C(CH$_3$)=CH—Ph | |
| 21 | O | —C(CH(CH$_3$)$_2$)=CH—Ph | |
| 22 | O | —C(C$_6$H$_4$Cl)=CH—Ph | |
| 23 | O | —CH$_2$CF$_3$ | |
| 24 | O | —(CH$_2$)$_3$CH$_2$Cl | $n_D^{20}$ 1.5128 |
| 25 | S | —CH$_3$ | |
| 26 | S | —CH$_2$CH(CH$_3$)$_2$ | |
| 27 | S | —(CH$_2$)$_6$CH$_3$ | |
| 28 | S | —CH$_2$—Ph | m.p. 42–45° C. |
| 29 | S | —CH$_2$—C$_6$H$_4$—F | |
| 30 | S | —CH$_2$—C$_6$H$_4$—Cl | |
| 31 | S | —(CH$_2$)$_4$CH$_2$Cl | |

Now the invention will be described in further detail with reference to Examples. The numbers of the compounds in the following Examples correspond to the numbers of the compounds in Table 1.

EXAMPLE 1

Preparation of 4-difluoromethoxyacetophenone (Compound No. 1)

In a reactor A, 54.4 g. of 4-hydroxyacetophenone was added to a solution of 17 g. of sodium hydroxide in 160 ml. of water and 400 ml. of dioxane.

On the other hand, in a reactor B, a solution of 80 g. of sodium hydroxide in 300 ml. of water and 360 ml. of dioxane was prepared. The reactor B was heated to 80° C. and Freon 22 gas was fed and the resulting difluorocarbene was fed through a polytetrafluoroethylene tube into the reactor A at room temperature. After feeding 200 g. of Freon 22 gas, the reactor A was cooled and 400 ml. of water and 500 ml. of ethyl ether were charged for extraction. The resulting organic phase was separated and dried over anhydrous sodium sulfate and ethyl ether was distilled off to obtain a crude product. The crude product was distilled under a reduced pressure to obtain 44.6 g. of 4-difluoromethoxyacetophenone having a boiling point of 98°–100° C./3 mmHg.

The chemical structure of the product was confirmed by the NMR spectrum:

$CDCl_3$, δ, p.p.m.; 2.52 (3H, s), 6.65 (1H, t, J=74.0 Hz), 7.13 (2H, d, J=9.0 Hz), 7.96 (2H, d, J=9.0 Hz)

EXAMPLE 2

Preparation of 4-difluoromethoxypropiophenone (Compound No. 2)

In accordance with the process of Example 1, 49.6 g. of 4-difluoromethoxy propiophenone (boiling point of 108°–109° C./3 mmHg) was produced as the product by using 60 g. of 4-hydroxypropiophenone instead of 54.4 g. of 4-hydroxyacetophenone.

The chemical structure of the product was confirmed by the NMR spectrum:

$CDCl_3$, δ, p.p.m.; 1.19 (3H, t, J=7.6 Hz), 2.95 (2H, q, J=7.6 Hz), 6.67 (1H, t, J=74.0 Hz), 7.16 (2H, d, J=9.0 Hz), 7.99 (2H, d, J=9.0 Hz)

EXAMPLE 3

Preparation of 4'-difluoromethoxy-2-phenylacetophenone (Compound No. 10)

A mixture of 17 g. of 4'-hydroxy-2-phenylacetophenone and 30 g. of sodium hydroxide in 40 ml. of water and 50 ml. of dioxane was heated at 70° to 80° C. and 22 g. of Freon 22 gas was fed into the solution during 1 hour while heating. After cooling the reaction mixture, 150 ml. of water and 150 ml. of ethyl ether were added to the reaction mixture and an organic phase was obtained by extraction. The organic phase was separated and dried over anhydrous sodium sulfate and ethyl ether was distilled off to obtain 17.6 g. of crystals of 4'-difluoromethoxy-2-phenylacetophenone. The compound was heated and dissolved, and then distilled under reduced pressure to obtain 16.8 g. of a fraction having a boiling point of from 140° to 150° C./0.5 mmHg. When left to stand at room temperature, the product was crystallized. The melting point was from 52° to 60° C.

The chemical structure of the product was confirmed by the NMR spectrum:

$CDCl_3$, δ, p.p.m.; 4.14 (2H, s), 6.52 (1H, t, J=74.0 Hz), 7.09 (2H, d, J=9.0 Hz), 7.24 (4H, bs), 7.98 (2H, d, J=9.0 Hz)

EXAMPLE 4

Preparation of 4'-difluoromethoxy-2-(4-chlorophenyl)-acetophenone (Compound No. 12)

In accordance with the process of Example 3, 16.8 g. of 4'-difluoromethoxy-2-(4-chlorophenyl)-acetophenone (melting point: 74.0°–76.0° C.) was obtained as the product by using 20 g. of 4'-hydroxy-2-(4-chlorophenyl)-acetophenone instead of 17 g. of 4'-hydroxy-2-phenylacetophenone.

The chemical structure of the product was confirmed by the NMR spectrum:

$CDCl_3$, δ, p.p.m.; 4.18 (2H, s), 6.59 (1H, t, J=74.0 Hz), 7.15 (2H, d, J=9.0 Hz), 7.20 (4H, bs), 7.98 (2H, d, J=9.0 Hz)

EXAMPLE 5

Preparation of 4-chloro-4'-difluoromethoxy chalcone (Compound No. 19)

Into 10 ml. of ethanol and 20 ml. of a 10% NaOH aqueous solution, 5.6 g. of 4'-difluoromethoxyacetophenone obtained by the process of Example 1 was added and then 4.2 g. of p-chlorobenzaldehyde was added to the mixture at room temperature while stirring. The mixture was stirred for 1 hour, whereupon crystals were precipitated. The mixture was then cooled to 0° C. and kept at 0° C. for 1 hour. The precipitated crystals were separated by filtration and washed twice with 20 ml. of water and once with 20 ml. cold ethanol and dried under a reduced pressure for 3 hours to obtain 8.4 g. of 4-chloro-4'-difluoromethoxy chalcone (melting point: 114°–115° C.).

The chemical structure of the product was confirmed by the NMR spectrum:

$CDCl_3$, δ, p.p.m.; 6.62 (1H, t, J=74.0 Hz), 7.22 (2H, d, J=9.0 Hz), 7.25–7.75 (6H, m), 8.05 (2H, d, J=9.0 Hz)

EXAMPLE 6

Preparation of 4'-difluoromethoxy-2-(phenyl)-isovalerophenone (Compound No. 16)

A solution of 43 g. of 4'-difluoromethoxy-2-phenylacetophenone obtained in Example 3 in 200 ml. of anhydrous tetrahydrofuran was cooled on an ice bath and mixed with 10 g. of sodium hydride (55% in mineral oil), and the mixture was stirred for 10 min. and then, 30 g. of isopropyl iodide was added dropwise. After the addition, the mixture was refluxed for 4 hours.

After the reaction, tetrahydrofuran was distilled off and 200 ml. of water and 200 ml. of ether were added to separate the organic phase by extraction. The water phase was treated with 100 ml. of ether by the extraction. The organic phases were mixed and dried over anhydrous sodium sulfate and the solvent was distilled off and the product was purified by a column chromatography (slica gel: benzene) to obtain 44 g. of the 4'-difluoromethoxy-2-(phenyl)-isovalerophenone ($N_D^{20}$=1.5312).

The chemical structure was confirmed by the NMR spectrum:

$CDCl_3$, δ, p.p.m.; 0.72 (3H, d, J=6.0 Hz), 0.98 (3H, d, J=6.0 Hz), 2.60 (1H, m), 4.11 (1H, d, J=9.0 Hz), 6.48 (1H, t, J=74.0 Hz), 7.06 (2H, d, J=9.0 Hz), 7.33 (5H, s), 7.98 (2H, d, J=9.0 Hz).

EXAMPLE 7

Preparation of
4'-difluoromethoxy-5-cyanovalerophenone (Compound No. 9)

Into a solution of 17 g. of NaOH in 160 ml. of water and 400 ml. of dioxane, 79.4 g. of 4'-hydroxy-5-chrolovalerophenone was added in Reactor A.

On the other hand, a solution of 80 g. of NaOH in 300 ml. of water and 360 ml. of dioxane was prepared in Reactor B. The reactor B was heated at 80° C., Freon-22 gas was fed and the resulting difluorocarbene was fed through a polytetrafluoroethylene tube (previously connected) into the Reactor A. In the Reactor A, the temperature was raised. After feeding 200 g. of Freon-22, the Reactor A was cooled and 400 ml. of water and 500 ml. of ethyl ether were charged to separate an organic phase by extraction. The organic phase was dried over anhydrous sodium sulfate, and ethyl ether was distilled off to obtain a crude product of 4'-difluoromethoxy-5-chlorovalerophenone.

Into 20 ml. of acetonitrile, 13 g. of the crude product was dissolved and 6.5 g. of potassium cyanide and 1 g. of 18-crown-6 were added to the solution and the mixture was refluxed for 3 hours. After cooling the reaction mixture, an insoluble matter was separated by filtration and 50 ml. of water was added to the filtrate. The product was extracted two times with 50 ml. of chloroform and the chloroform phase was dried over anhydrous sodium sulfate and the solvent was distilled off under a reduced pressure to obtain 12 g. of the crude product. The crude product was purified by column chromatography (silica gel: ethyl acetate : benzene = 1:9 as developer) to obtain 9 g. of the 4'-difluoromethoxy 5-cyanovalerophenone ($N_D^{20}$ 1.5045).

The chemical structure was confirmed by the NMR spectrum:

CDCl$_3$, δ, p.p.m.; 1.60–2.20 (4H, m), 2.39 (2H, t, J=6.0 Hz), 3.00 (2H, t, J=6.0 Hz), 6.62 (1H, t, J=74.0 Hz), 7.18 (2H, d, J=9.0 Hz), 7.98 (2H, d, J=9.0 Hz)

EXAMPLE 8

Preparation of
4'-difluoromethylthio-2-phenylacetopheone (Compound No. 28)

Into a 200 ml. four necked flask equipped with a dropping funnel and a condenser, 2.4 g. of magnesium (0.1 mol) and 20 ml. of dried ethyl ether were introduced and the internal atmosphere of the flask was replaced by nitrogen gas. A solution prepared by dissolving 17.1 g. (0.1 mol) of benzyl bromide in 50 ml. of dried ethyl ether, was dropwise added thereto at room temperature to obtain a Grignard reagent.

The this solution, a solution prepared by dissolving 18.5 g. (0.1 mol) of p-difluoromethylthio benzonitrile in 50 ml. of ethyl ether, was dropwise added at room temperature and after completion of the dropwise addition, the mixture was refluxed for one hour under heating. After cooling, the solution was poured into ice water, and 20 ml. of 1N HCl was added thereto. The mixture was extracted twice with 100 ml. of ethyl ether. The organic phase was dried over anhydrous sodium sulfate, and ethyl ether was distilled off to obtain 23 g. of a crude product.

The crude product was purified by silica gel column chromatography (developed with benzene), and further recrystallized from n-hexane, whereupon 15 g. of 4'-difluoromethylthio-2-phenylacetophenone was obtained (melting point: 42°-45° C.).

The chemical structure was confirmed by the NMR spectrum:

CDCl$_3$, δ, p.p.m.; 4.18 (s, 2H), 6.80 (t, J=56.0 Hz, 1H), 7.22 (s, 5H), 7.54 (d, J=8.0 Hz, 2H), 7.94 (d, J=8.0 Hz, 2H)

Now, the insecticidal activities of the compounds prepared from the compounds of the present invention will be described in the following Reference Examples.

REFERENCE EXAMPLE 1

(1) 17.5 g. of crude Compound No. 10 obtained by Example 3 was added to a mixture comprising 0.9 ml. of piperidine, 0.9 ml. of acetic acid, 25 ml. of 37% formaline and 180 ml. of methyl alcohol, and the mixture was refluxed and reacted for 3 hours. The reaction mixture was concentrated under reduced pressure, and then 150 ml. of water and 200 ml. of chloroform were added thereto for liquid phase separation, whereupon an organic phase was obtained. The organic phase was dried over anhydrous sodium sulfate and chloroform was distilled off to obtain 18.0 g. of 4'-difluoromethoxy-2-phenylacrylophenone ($N_D^{20}$:1.5819). Then, 17.5 g. of this product and 8 ml. of hydrazine hydrate were refluxed in ethyl alcohol for reaction for 3 hours. After the reaction, the reaction mixture was concentrated under reduced pressure, and 80 ml. of water and 100 ml. of chloroform were added, whereupon an organic phase was obtained. After drying the organic phase over anhydrous sodium sulfate, chloroform was distilled off, whereupon 17.5 g. of 3-(4-difluoromethoxyphenyl)-4-phenyl-2-pyrazoline (melting point: 65°-75° C.) was obtained. Then, 5.8 g. of the compound thus obtained and 3.1 g. of 4-chlorophenylisocyanate were added to dried ethyl ether and reacted for 6 hours under reflux. After cooling the reaction mixture, precipitated crystals were collected by filtration, whereby 5.3 g. of the product was obtained. This product was confirmed by the NMR spectrum to be 1-(4-chlorophenyl-carbamoyl)-3-(4-difluoromethoxyphenyl)-4-phenyl-2-pyrazoline. (Melting point: 147.0°-148.0° C.).

(2) Contact test for killing Common cutworm:

Leaves of cabbage were dipped for 10 second in aqueous emulsion containing 1.25 ppm of the compound prepared by the above process. The leaves were taken out and dried in air and put in a Petri dish. Common cutworms (second instar) were put in the Petri dish, and a perforated cover was placed on the Petri dish. The Petri dish was maintained in a constant temperature room at 25° C., and upon expiration of 48 hours, the percent mortality was determined.

It was found that the percent mortality was 100%.

REFERENCE EXAMPLE 2

In the same manner as in Reference Example 1, compounds were prepared from the compounds of the present invention, and with use of aqueous emulsions containing 100 ppm of the compounds thus prepared, the percent mortality of Common cutworms was examined. The results thereby obtained are shown in Table 2.

TABLE 2

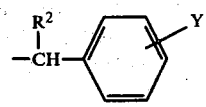

| Starting materials (Compounds of the present invention) | R⁸ | R⁹ and R¹⁰ | X | U | Mortality (%) |
|---|---|---|---|---|---|
| 1 | H | H | O | 4-Cl | 100 |
| 2 | CH₃ | H | O | 4-CF₃ | 100 |
| 4 | CH(CH₃)₂ | H | O | 4-SCF₃ | 100 |
| 7 | (CH₂)₅CH₃ | H | O | 4-CF₃ | 100 |
| 9 | (CH₂)₃CN | H | O | 4-SCF₃ | 100 |
| 11 | –C₆H₄–F | H | O | 4-Cl | 100 |
| 12 | –C₆H₄–Cl | H | O | 4-Br | 100 |
| 16 | –C₆H₅ | (CH₃)₂ | O | 4-OCF₃ | 100 |
| 18 | H | –C₆H₅ | O | 4-Cl | 100 |
| 19 | H | –C₆H₄–Cl | O | 4-Cl | 100 |
| 28 | –C₆H₅ | H | S | 4-Cl | 100 |

We claim:

1. Ketone derivatives represented by the general formula (I)

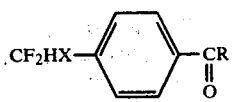

where R is —CH₂R¹ (where R¹ is a hydrogen atom or an alkyl group), a halogen-substituted alkyl group, a cyano-substituted alkyl group, a cyclopropyl group,

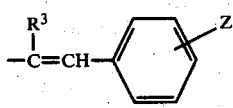

(where R² is a hydrogen atom or an alkyl group and Y is a hydrogen atom or a halogen atom) or $$-\underset{R^3}{\overset{}{C}}=CH-\!\!\!\!\!\!\bigcirc\!\!\!\!\!\!-Z$$

(where R³ is a hydrogen atom, an alkyl group, a phenyl group or a halogen-substituted phenyl group, and Z is a hydrogen atom or a halogen atom), and X is an oxygen atom or a sulfur atom.

2. Ketone derivatives according to claim 1 which are represented by the general formula (II)

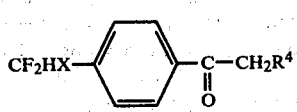

where R⁴ is a hydrogen atom, an alkyl group having from 1 to 9 carbon atoms or

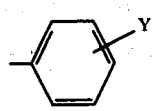

(where X is a hydrogen atom or a halogen atom), and X is an oxygen atom or a sulfur atom.

3. Ketone derivatives according to claim 2 wherein X in the general formula (II) is an oxygen atom.

4. 4-Difluoromethoxy acetophenone according to claim 1.

5. 4-Difluoromethoxy propiophenone according to claim 1.

6. 4-Difluoromethoxy isovalerophenone according to claim 1.

7. 4′-Difluoromethoxy-2-phenylacetophenone according to claim 1.

8. 4′-Difluoromethoxy-2-(4-chlorophenyl)-acetophenone according to claim 1.

9. 4′-Difluoromethoxy-2-(4-fluorophenyl)-acetophenone according to claim 1.

* * * * *